US007102132B2

(12) United States Patent
Ludviksson

(10) Patent No.: US 7,102,132 B2
(45) Date of Patent: Sep. 5, 2006

(54) PROCESS MONITORING USING INFRARED OPTICAL DIAGNOSTICS

(75) Inventor: Audunn Ludviksson, Scottsdale, AZ (US)

(73) Assignee: Tokyo Electron Limited, Tokyo (JP)

( * ) Notice: Subject to any disclaimer, the term of this patent is extended or adjusted under 35 U.S.C. 154(b) by 190 days.

(21) Appl. No.: 10/507,201

(22) PCT Filed: Mar. 17, 2003

(86) PCT No.: PCT/US03/06710

§ 371 (c)(1),
(2), (4) Date: Sep. 14, 2004

(87) PCT Pub. No.: WO03/081216

PCT Pub. Date: Oct. 2, 2003

(65) Prior Publication Data

US 2005/0082482 A1    Apr. 21, 2005

Related U.S. Application Data

(60) Provisional application No. 60/365,529, filed on Mar. 20, 2002.

(51) Int. Cl.
*G01N 21/35*    (2006.01)
(52) U.S. Cl. ............... 250/343; 250/341.4; 250/339.13
(58) Field of Classification Search ............... 250/343, 250/339.01, 339.07, 339.13, 341.4
See application file for complete search history.

(56) References Cited

U.S. PATENT DOCUMENTS

| 5,131,752 | A | 7/1992 | Yu et al. |
| 5,313,044 | A | 5/1994 | Massoud et al. |
| 5,793,042 | A | 8/1998 | Quick |
| 5,841,533 | A | 11/1998 | Atkinson |
| 5,880,850 | A | 3/1999 | McAndrew et al. |
| 5,897,378 | A * | 4/1999 | Eriguchi ..................... 438/707 |
| 5,900,633 | A | 5/1999 | Solomon et al. |
| 6,366,346 | B1 | 4/2002 | Nowak et al. |
| 6,455,437 | B1 | 9/2002 | Davidow et al. |
| 2002/0158202 | A1 * | 10/2002 | Webber et al. ......... 250/339.13 |

FOREIGN PATENT DOCUMENTS

| WO | 01/42767 | 6/2001 |
| WO | WO 2003081216 A2 * | 10/2003 |

* cited by examiner

*Primary Examiner*—Albert Gagliardi
(74) *Attorney, Agent, or Firm*—Oblon, Spivak, McClelland, Maier & Neustadt, P.C.

(57) ABSTRACT

A method and apparatus for real-time monitoring of the substrate and the gaseous process environment in a semiconductor process step is described. The method uses infrared spectroscopy for in-situ analysis of gaseous molecular species in the process region and characterization of adsorbed chemical species on a substrate. The process monitoring can be applied to endpoint- and fault detection in etching and deposition processes, in addition to chamber cleaning and chamber condition steps.

37 Claims, 6 Drawing Sheets

PROCESS MONITORING USING INFRARED OPTICAL DIAGNOSTICS

CROSS-REFERENCE TO RELATED APPLICATIONS

This application claims priority and is related to U.S. Application Ser. No. 60/365,529, filed on Mar. 20, 2002. This application is related to U.S. Application Ser. No. 60/352,546, filed Jan. 31, 2002 and Ser. No. 10/096,932, filed Mar. 14, 2002. The contents of all of these applications are incorporated herein by reference in their entirety.

BACKGROUND OF THE INVENTION

1. Field of the Invention

The present invention relates to real-time in-situ monitoring of semiconductor processing. The invention uses infrared spectroscopy to monitor the substrate and the gaseous environment during a process.

2. Background of the Invention

Advanced process control that involves in-situ process monitoring and fault detection in semiconductor manufacturing is essential for reproducible production of complex structures. Introduction of new materials and smaller dimensions into integrated circuits results in the need for improved process monitoring to assure process compliance and cost reduction.

In typical etching and film deposition processes, the wafer parameters are measured after the processing steps using test wafers. If the measured parameters are not within the desired tolerances, the process parameters are adjusted and more test wafers are run and measured to verify the corrective measures. This method of post-process analysis is time consuming, inefficient, and becomes increasingly more expensive as the wafer size increases. In addition to manufacturing runs, process development and yield ramping increase the number of test wafers that require post-process analysis.

These drawbacks can be reduced using real-time tool and process monitoring. In order to minimize the number of wafers that are run on a faulty process, it is necessary to know if critical parameters are outside specifications during processing. If a process is stopped for troubleshooting, a wafer can be examined ex-situ for physical properties such as film thickness, density and composition. The use of real-time process monitoring will not eliminate the need for conventional ex-situ metrology, but will allow better process control and reduce the number of test wafers.

Real-time monitoring during etching and film deposition steps should (1) yield detailed information on the various chemical components in the gaseous environment and (2) in many cases, preferably also offer means for monitoring and analyzing chemical species on the substrate surface. The acquired data can be used to improve the process by optimizing process conditions, detecting trends of departure from target values and allow early recognition of a possible catastrophic failure of the process equipment. In addition to etching and film deposition processes, chamber cleaning and chamber conditioning processes require in-situ monitoring for improved process control.

A variety of spectroscopic methods have been applied to real-time process monitoring. These analytical methods allow qualitative and quantitative analysis of the gaseous chemical species through the use of techniques such as mass spectroscopy (MS) and optical emission spectroscopy (OES). These techniques provide information on the identity and concentration of gaseous species during the manufacturing process, which in turn can be correlated to various physical properties of the processed substrates.

OES is a widely used method for process monitoring and control in semiconductor processing. OES is a non-invasive technique that has an extremely wide dynamic range and can perform process control (e.g., endpoint detection, etch rate, or partial pressure control) and diagnostics concurrently. However, it cannot be used in non-plasma processes such as film deposition, and the optical emission spectrum from plasma processes can be very complicated. Furthermore, OES does not provide direct information about the substrate during a process step.

The aforementioned disadvantages using post-process analysis show that there is a need for non-invasive methods for monitoring of semiconductor processes that allow for comprehensive analysis of the gaseous environment and the substrate during a process step. The real-time results are correlated to various physical properties of the substrates and can reduce the use of test wafer reiterative monitoring methods.

SUMMARY OF THE INVENTION

It is a primary object of the present invention to provide an apparatus and a method for in-situ process monitoring and control of a semiconductor processing step using infrared (IR) spectroscopy.

The above and other objects are achieved, according to the present invention, by using infrared transmission absorption spectroscopy (ITAS) or Fourier transform ITAS (FT-ITAS) to analyse and monitor the gaseous environment in the chamber process region. In an alternate embodiment, reflection-absorption infrared spectroscopy (RAIRS) or FT-RAIRS is used to monitor chemical species that are adsorbed on the substrate in a semiconductor processing step.

It is a further object of the present invention to correlate resulting gaseous environments in the process chamber with physical properties of the processed wafers and to improve the process by optimizing process conditions and detecting trends of departure from target values.

BRIEF DESCRIPTION OF THE DRAWINGS

A more complete appreciation of the invention and many of the attendant advantages thereof will become readily apparent with reference to the following detailed description, particularly when considered in conjunction with the accompanying drawings, in which.

DETAILED DESCRIPTION OF THE INVENTION

In general, the present invention provides an apparatus and a method for carrying out real-time in-situ process monitoring during a semiconductor process using infrared spectroscopy. The process can comprise deposition or etching steps that are carried out in the presence of a plasma or by thermal reactions in the absence of a plasma. In the Figures, like reference numbers are used to indicate like elements throughout.

One aspect of the current invention is detecting and monitoring the gaseous environment in the processing system during etching or deposition steps. This is carried out using FT-ITAS to identify and monitor gaseous species of interest in the processing system and detecting trends of departure from target values. Another aspect of the current invention is applying FT-ITAS to chamber cleaning and chamber conditioning. Yet another aspect of the current invention is using FT-RAIRS for identifying and monitoring chemical species adsorbed on a substrate during etching or deposition steps.

Infrared spectroscopy is a well-established analytical method and is ideal for semiconductor process monitoring, because it can be used in both vacuum or non-vacuum environments and can provide a wealth of valuable information during a process step. The parameters that are monitored with the present invention include, but are not limited to, concentration of gaseous species, ratios of gaseous species, gas flows, pressure, and gas impurities. These parameters can be correlated with prior process results and experience.

In order to absorb infrared radiation, a molecule must undergo a net change in dipole moment as a consequence of its vibrational or rotational motion. Only under these circumstances can the alternating electrical field of the infrared radiation interact with the molecule and cause changes in the amplitude of one of its motions. No net change in dipole moment occurs during the vibration or rotations of homonuclear species such as $O_2$, $N_2$ or $Cl_2$; consequently, such molecules cannot absorb infrared radiation. This also applies to atomic species, such as Ar, O or Cl.

Figure 1A:
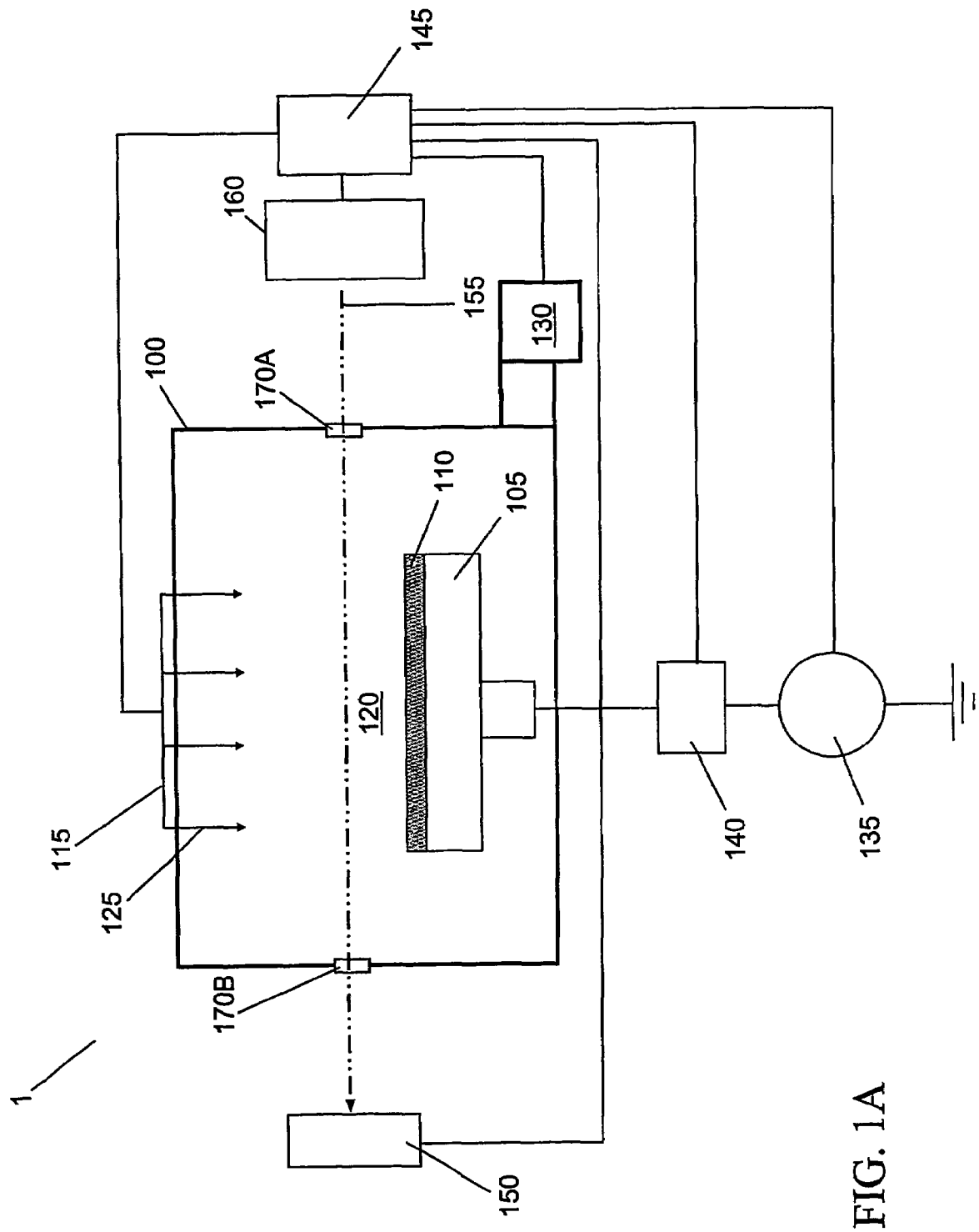
FIG. 1A is a simplified block diagram of an infrared diagnostic system in communication with a plasma processing system according to the present invention.

FIG. 1A is a simplified block diagram of an infrared diagnostic system in communication with a plasma processing system according to the present invention. Infrared radiation is transmitted through the processing zone and the measured attenuation, due to infrared absorption of gaseous species in the processing zone, is proportional to the partial pressures of the gaseous species. Monitoring the infrared radiation provides fast real-time information of changes that occur in the process environment. In FIG. 1A, device 1 is depicted and comprises a plasma processing device with a chamber 100, substrate holder 105, upon which substrate 110 to be processed is affixed, and gas injection system 115. Chamber 100 can be configured to facilitate the generation of plasma in processing region 120 adjacent a surface of substrate 110, wherein plasma is formed via collisions between heated electrons and an ionizable gas. An ionizable gas or mixture of gases 125 is introduced via gas injection system 115 and the process pressure is adjusted. For example, a gate valve (not shown) can be used to throttle the vacuum pumping system 130. Desirably, plasma is utilized to create materials specific to a pre-determined materials process, and to aid either the deposition of material to substrate 110 or the removal of material from the exposed surfaces of substrate 110.

Substrate 110 can be transferred into and out of chamber 100 through a slot valve (not shown) and chamber feed-through (not shown) via robotic substrate transfer system where it is received by substrate lift pins (not shown) housed within substrate holder 105 and mechanically translated by devices housed therein. Once substrate 110 is received from the substrate transfer system, it is lowered to an upper surface of the substrate holder 105.

In an alternate embodiment, substrate 110 can be affixed to substrate holder 105 via an electrostatic clamp (not shown). Furthermore, substrate holder 105 further includes a cooling system including a re-circulating coolant flow that receives heat from substrate holder 105 and transfers heat to a heat exchanger system (not shown), or when heating, transfers heat from the heat exchanger system. Moreover, gas may be delivered to the backside of the substrate to improve the gas-gap thermal conductance between substrate 110 and substrate holder 105. Such a system is utilized when temperature control of the substrate is required at elevated or reduced temperatures. For example, temperature control of the substrate may be useful at temperatures in excess of the steady-state temperature achieved due to a balance of the heat flux delivered to substrate 110 from the plasma and the heat flux removed from substrate 110 by conduction to the substrate holder 105. In other embodiments, heating elements, such as resistive heating elements, or thermoelectric heaters/coolers are included.

In the embodiment shown in FIG. 1A, substrate holder 105 further serves as an electrode through which radio frequency (RF) power is coupled to plasma in processing region 120. For example, substrate holder 105 can be electrically biased at a RF voltage via transmission of RF power from RF generator 135 through impedance match network 140 to substrate holder 105. The RF bias serves to heat electrons and, thereby, form and maintain plasma. In this configuration, the system operates as a reactive ion etch (RIE) reactor, wherein the chamber and the upper gas injection electrode serve as ground surfaces. A typical frequency for the RF bias can range from 1 MHz to 100 MHz and is preferably 13.56 MHz.

In an alternate embodiment, RF power is applied to the substrate holder electrode at multiple frequencies. Furthermore, impedance match network 140 serves to maximize the transfer of RF power to plasma in processing chamber 10 by minimizing the reflected power. Match network topologies (e.g. L-type, π-type, T-type, etc.) and automatic control methods are known in the art.

With continuing reference to FIG. 1A, process gas 125 is introduced to processing region 120 through gas injection system 115. Gas injection system 115 can include a showerhead, wherein process gas 125 is supplied from a gas delivery system (not shown) to processing region 120 through a gas injection plenum (not shown), a series of baffle plates (not shown) and a multi-orifice showerhead gas injection plate (not shown).

Vacuum pump system 130 preferably includes a turbomolecular vacuum pump (TMP) capable of a pumping speed up to 5000 liters per second (and greater). For example, a gate valve can be used for throttling the chamber pressure. In conventional plasma processing devices utilized for dry plasma etch, a 1000 to 3000 liter per second TMP is employed. TMPs are useful for low pressure processing, typically less than 50 mTorr. At higher pressures, the TMP pumping speed falls off dramatically. For high pressure processing (i.e. pressures greater than 100 mTorr), a mechanical booster pump and a dry roughing pump can be used.

Controller 145 includes a microprocessor, a memory, and a digital I/O port capable of generating control voltages sufficient to communicate and activate inputs to plasma processing system 1 as well as monitor outputs from plasma processing system 1. Moreover, controller 145 is coupled to and exchanges information with RF generator 135, impedance match network 140, gas injection system 115 and vacuum pump system 130. A program stored in the memory is utilized to control the aforementioned components of plasma processing system 1 according to a stored process recipe. Furthermore, controller 145 is capable of controlling the components of the infrared optical system and receiving outputs from detector 150. Alternatively, the setup in FIG. 1 can consist of multiple controllers that are assigned to different tasks. One example of controller 145 is a digital signal processor (DSP), available from Texas Instruments, Dallas, Tex.

An infrared optical monitoring system is also depicted in FIG. 1A. Infrared radiation 155 is generated by spectrometer 160 and passed through a light transmissive window 170A, and a portion of the transmitted light passes through a second transmissive window 170B. Preferably, the spectrometer 160 emits infrared light in spectral regions where the molecules in the processing chamber absorb most strongly. In particular, light sources that emit light at wavelengths greater than about 2 microns are preferred. The source of infrared radiation is typically an inert solid heated electrically to temperatures between 1,500 and 2,000K. Continuous radiation approximating that of a black body results with a maximum radiant intensity between 1.7 and 2 µm (5900 to 5000 $cm^{-1}$).

The spectrometer 160 is preferably a Fourier transform spectrometer that creates a beam of modulated infrared light. Significant gain in signal-to-noise ratio can be achieved using Fourier transform techniques, which are effective in extracting weak signals from a noisy environment by signal averaging. The spectrometer can contain the classical Michelson interferometer for modulating the infrared radiation, wherein a beam of radiation is split into two beams of nearly equal powers and then recombined in such a way that intensity variations of the combined beam can be measured by detector 150 as a function of differences in the lengths of the paths of the two halves (interferogram). The spectrometer may either be fixedly attached to the system or "wheeled up" to the window 170A as needed.

Infrared Fourier transform spectroscopy consists of recording the interferogram and then mathematically transforming the acquired spectral information to the conventional frequency domain where the radiant intensity is displayed as a function of radiant frequency. The transformation is performed using a high-speed controller capable of performing mathematical analysis. For a transparent sample through which infrared light passes, this type of analysis produces an absorption curve where the intensity of an absorption feature is proportional to the amount of a particular absorbing species present in the sample. The absorbance can be converted to concentration of the molecular species by controller 145 using known calibration data.

Figure 1B:
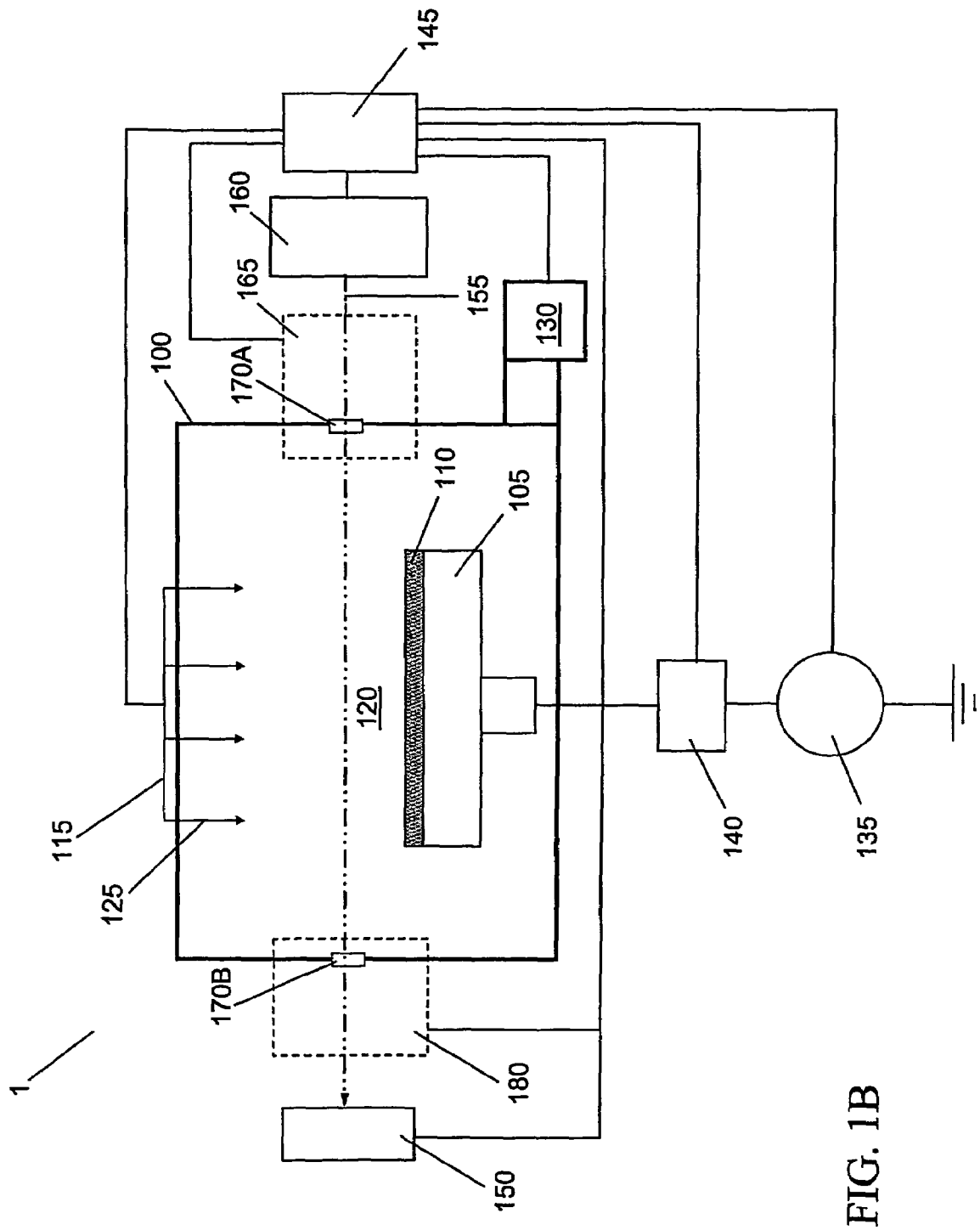
FIG. 1B is a simplified block diagram of an infrared diagnostic system in communication with a plasma processing system according to the present invention.

In an alternate embodiment, the system further comprises at least one optical system, as shown in FIG. 1B. Optical assembly 165 comprises the light transmissive window 170 and optional mirrors and lenses that are used to shape and direct infrared radiation 155 into processing chamber 100. The optical monitoring system in FIG. 1B can be configured such that infrared radiation 155 travels through processing chamber 100 above substrate 110, thereby interacting with gaseous molecular species in the chamber environment, exits through an optical assembly 180 (including a transmissive window 170B) and directed onto optical sensor 150. There is preferably a close match between the size of the beam ($\sim 1 \times 1$ $mm^2$) at the sensor and the dimensions of the sensor active area ($\sim 1 \times 1$ $mm^2$). In an alternate embodiment, at least one of the transmissive windows 170A and 170B acts as a lens itself.

The window material in transmissive windows 170A and 170B can comprise KBr or NaCl. The spectrometer and the entire optical path external to the process chamber can be sealed for evacuation or for purging atmospheric $H_2O$ and $CO_2$ with inert gas to eliminate or significantly reduce the contribution of these gases to the absorption spectra. Alternatively, the contribution of infrared absorption due to atmospheric gases in the optical path can be subtracted from the measured signal.

Sensor 150 responds to light of the same wavelength as emitted by light source 160. Suitable sensors can comprise liquid nitrogen cooled mercury-cadmium-telluride (MCT) or indium-antimonide (InSb) detectors, or a room temperature deuterated triglycine sulfate (DTGS) detector. These detectors are well known in the art and are commercially available. Furthermore, appropriate optics for infrared radiation, such as mirrors, lenses and windows are well known in the art. Sensor electronics receive the output from the detector and generate an electrical output that is proportional to the absorbance of light at one or more wavelengths.

According to one aspect of the invention, the plasma processing system is suitable to run vacuum processes, such as etching, sputtering, ion implantation or chemical vapor deposition processes. In addition, the current invention can be applied to chamber cleaning and chamber conditioning.

Common etch processes (e.g., for polysilicon, polycide, and silicon) produce etch products that may contain carbon, silicon, silicon oxides, and nitrides as well as chlorides, bromides, and fluorides from the etch chemistries used. These etch products may accumulate on the chamber walls and generate particle contamination. Furthermore, the chamber deposits may affect etch processes in areas such as etch rate, etch profile, critical-dimension control and, and the remaining wafer oxide. Therefore, chambers must be periodically scheduled for cleaning. The cleaned systems are then subject to re-qualification and chamber conditioning that involves processing multiple wafers until stable acceptable results are obtained.

Monitoring the infrared absorption of gaseous impurities and reaction products as detrimental chamber deposits are volatilized and removed during a cleaning process allows for determination of the endpoint of the chamber cleaning. Chamber conditioning after a chamber cleaning often involves processing multiple wafers to reach process steady-state conditions. Analogously, monitoring the gaseous environment during chamber conditioning can indicate when a steady-state condition has been reached.

In an alternate embodiment, the processing chamber can comprise a plurality of light transmissive windows for monitoring different areas in the process chamber. These windows can be arranged vertically or horizontally with respect to the plane formed by the substrate surface. The process monitoring can be carried out using a translatable optical mount to control the movement of the optical assembly so that the infrared beam is in optical communication with a particular transmissive window. Although the use of plurality of windows is described herein, in an alternative embodiment, a single window runs the length of the portion of the chamber to be examined, and the characteristics of the process environment and the substrate are simply monitored at multiple locations along the window. Alternatively, the optical assembly can be connected to a plurality of transmissive windows through the use of multiple optical fibers.

An infrared light beam that travels through the process zone close to substrate can reveal different information than a beam traveling through the process zone close to the gas injection (or upper electrode) area. In the case of an etching process, depletion of the reactant gas can be observed near the substrate surface due to reaction of the reactant gas with the substrate.

Figure 2:
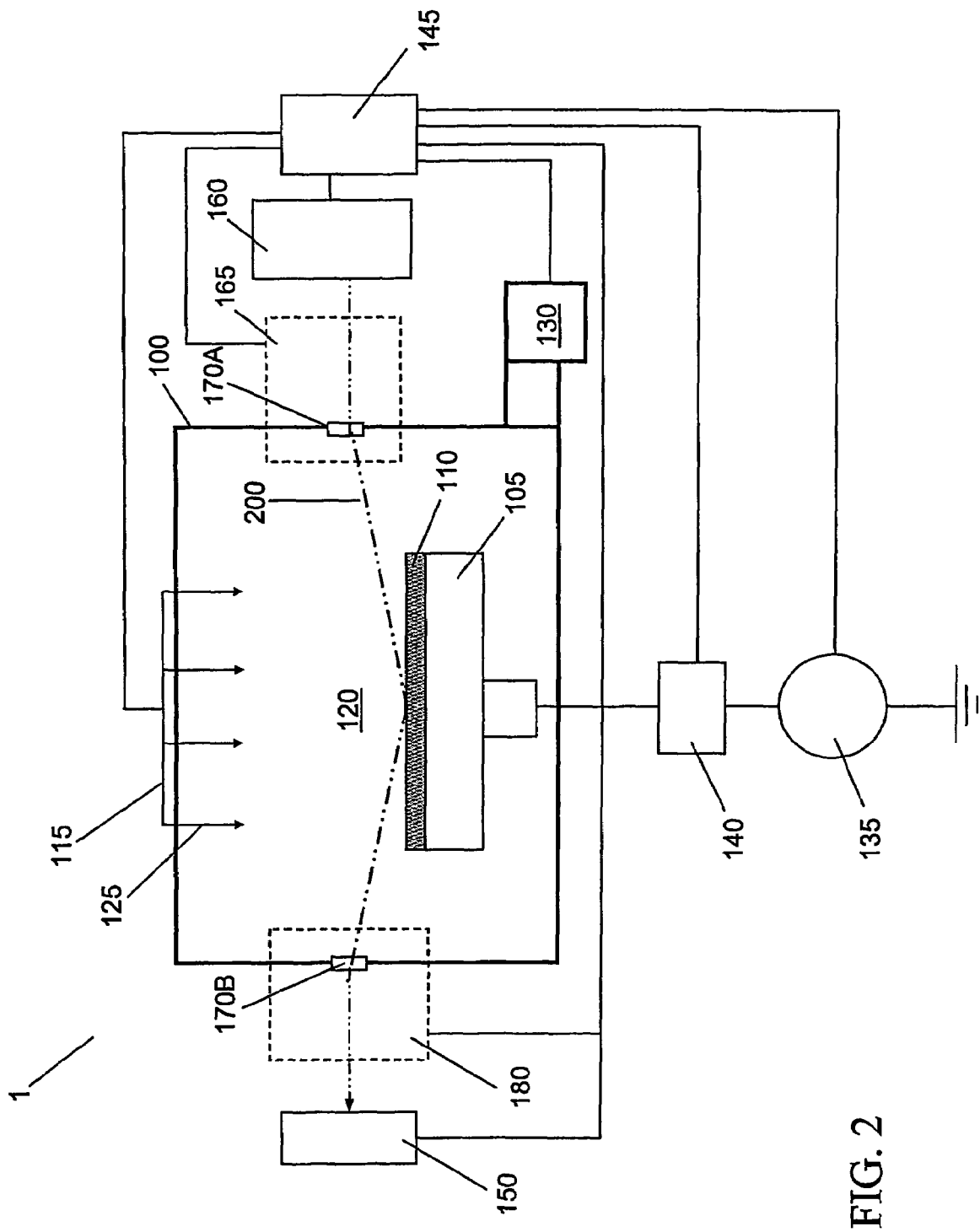
FIG. 2 is a simplified block diagram of a second infrared diagnostic system in communication with a plasma processing system according to the present invention.

FIG. 2 is a simplified block diagram of a second infrared diagnostic system in communication with a plasma processing system according to the present invention. The diagram describes a setup for monitoring adsorbed chemical species on a substrate during a processing step using RAIRS. Unlike in the setup in FIGS. 1A and 1B, where a beam of infrared radiation travels through the processing zone above the substrate, a beam of infrared radiation in FIG. 2 is reflected off the smooth substrate surface at grazing incidence (~85°). According to the setup illustrated in FIG. 2, infrared light beam 200 enters the processing chamber through light transmissive window 170A, interacts with adsorbed chemical species and reflects off substrate 110, exits the chamber through light transmissive window 170B, is re-focused by optical assembly 180 and is directed onto detector 150.

The spectrum of infrared light reflected from the surface shows absorption peaks at infrared frequencies that are characteristic of the adsorbed molecules and their chemical bond to the surface. The use of FT-RAIRS allows for high-resolution vibrational spectroscopy of adsorbed molecules with very high sensitivity that is sufficient to probe adsorbates species at monolayer concentrations.

In FT-RAIRS, vibrational molecular motion that contains vibrations whose oscillating dipole moment lies perpendicular (normal) to the substrate surface are IR active and give rise to observable absorption. This is because the incident and reflected p-polarised components of the radiation superimpose constructively (add together), enhancing the signal, whereas the s-polarised components cancel each other out as they undergo a phase change on reflection from the surface. Importantly, the reflected signal that is due to adsorbed species can readily be distinguished from gas-phase absorptions using polarization methods. For example, the exiting beam is p-polarized using a ZnSe wire grid polarizer which is located in optical assembly 180 and positioned to accept only radiation that is polarized parallel to the plane of incidence and contains the vibrational data associated with adsorbed surface species.

The highly sensitive nature of vibrational interactions and the extremely fine resolution of FT-RAIRS can enable deciphering of spectral line shifts and widths in the determination of bonding geometries, chemisorption methods, molecular fragmentation, bond site inhomogeneities, inter-adsorbate interactions and vibrational energy transfer mechanisms. The rate of energy transfer determines the lifetimes of adsorbate vibrational states and hence the line widths of the vibrational peaks. FT-RAIRS can thus be used to determine accurately the lineshapes of adsorbate vibrations as a sensitive probe of vibrational relaxation and lifetimes.

The method of spectral interpretation and characterization invariably involves the comparison of surface adsorbed spectra with that of the gas phase; as well comparison between the clean surface and the adsorbed surface, and ultimately, the comparison of spectra of the adsorbed surface, under different experimental conditions. For example, the infrared absorption frequencies for CO range from ~2143 $cm^{-1}$ for gas phase CO, 2100–1920 $cm^{-1}$ for terminally bonded CO (bonded to one substrate atom), and <1920 $cm^{-1}$ for bridge bonded CO (bonded to two substrate atoms). For a number of practical reasons, low frequency modes (<600 $cm^{-1}$) are not generally observable. This means that it is usually not possible to see the vibration of the substrate-adsorbate bond and attention is instead concentrated on the intrinsic vibrations of the adsorbate species in the range 600–3600 $cm^{-1}$.

In general, the identification of important gaseous species and monitoring ratios of gaseous species provides a fingerprint of important process variables and offers an early warning system. This invention is capable of alerting a monitoring system or user to changes when process window limits are approached that can cause a process to be out of specification. The invention can also be utilized to determine whether or not a given run has produced a satisfactory result. This can be done by comparison of the run profile to a collection of gas profiles that represent, based on previously established criteria, successful or unsuccessful runs. If an unsuccessful run is encountered, the invention provides means for classifying the fault, followed by terminating the process or correcting the fault.

Endpoint detection is one of the most important areas of real-time monitoring for etch processes. As a film being etched starts to clear, the increase in etchant species, such as $CF_2$ in the case of an oxide film, and the decrease of reactant products, such as CO (in the oxide case), cause the absorption intensities of these gaseous species to increase and decrease, respectively. By measuring the light absorption change associated with chemical species in the process environment, an endpoint time can be determined and the end control signal terminates the process step. In addition to a monitoring change in the gaseous environment, characteristics of adsorbed surface species can change during the transition from one type of surface to another, due to different adsorbate species and alternate bonding configurations.

Figure 3A:
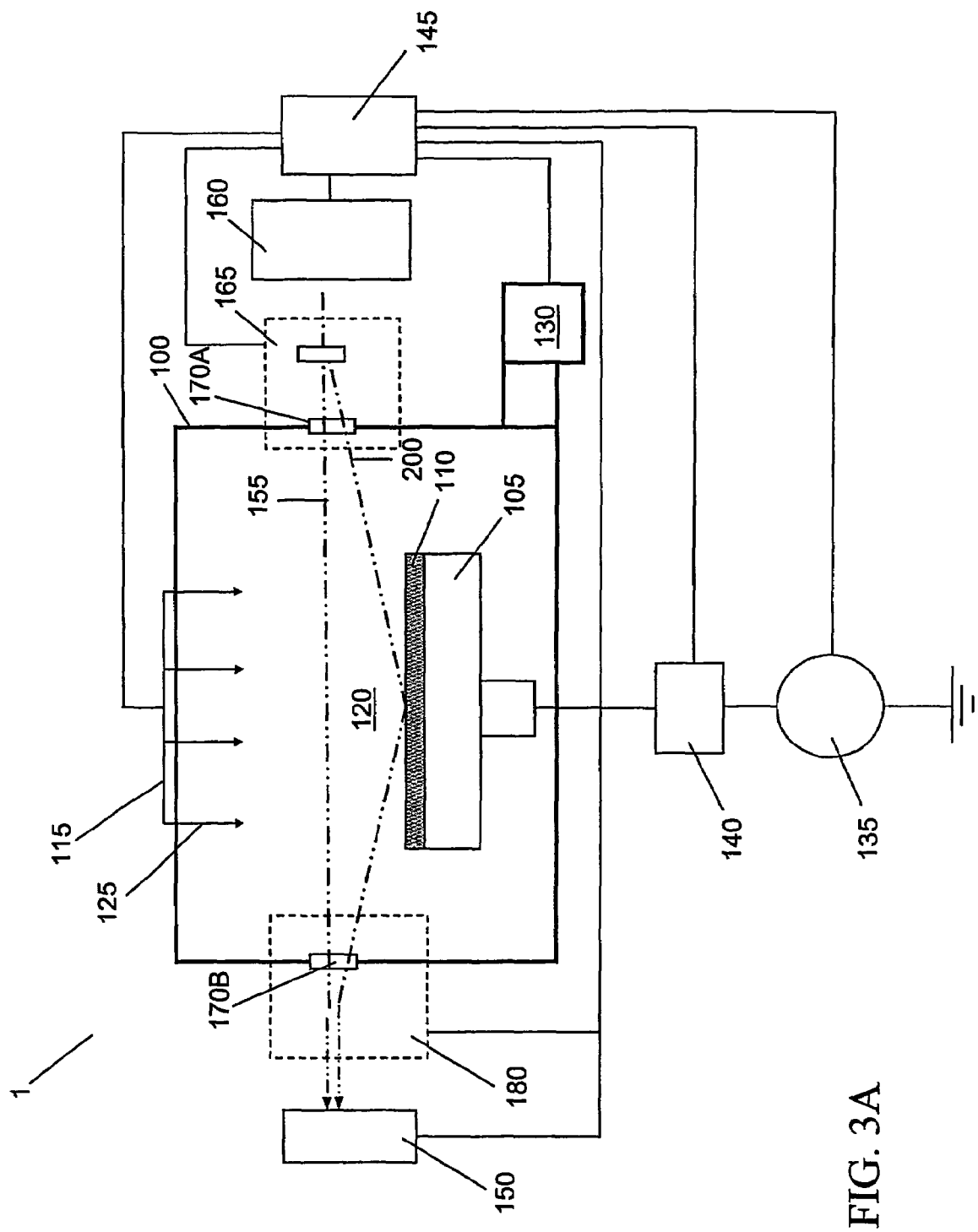
FIG. 3A is a simplified block diagram of third infrared diagnostic system in communication with a plasma processing system according to the present invention.
Figure 3B:
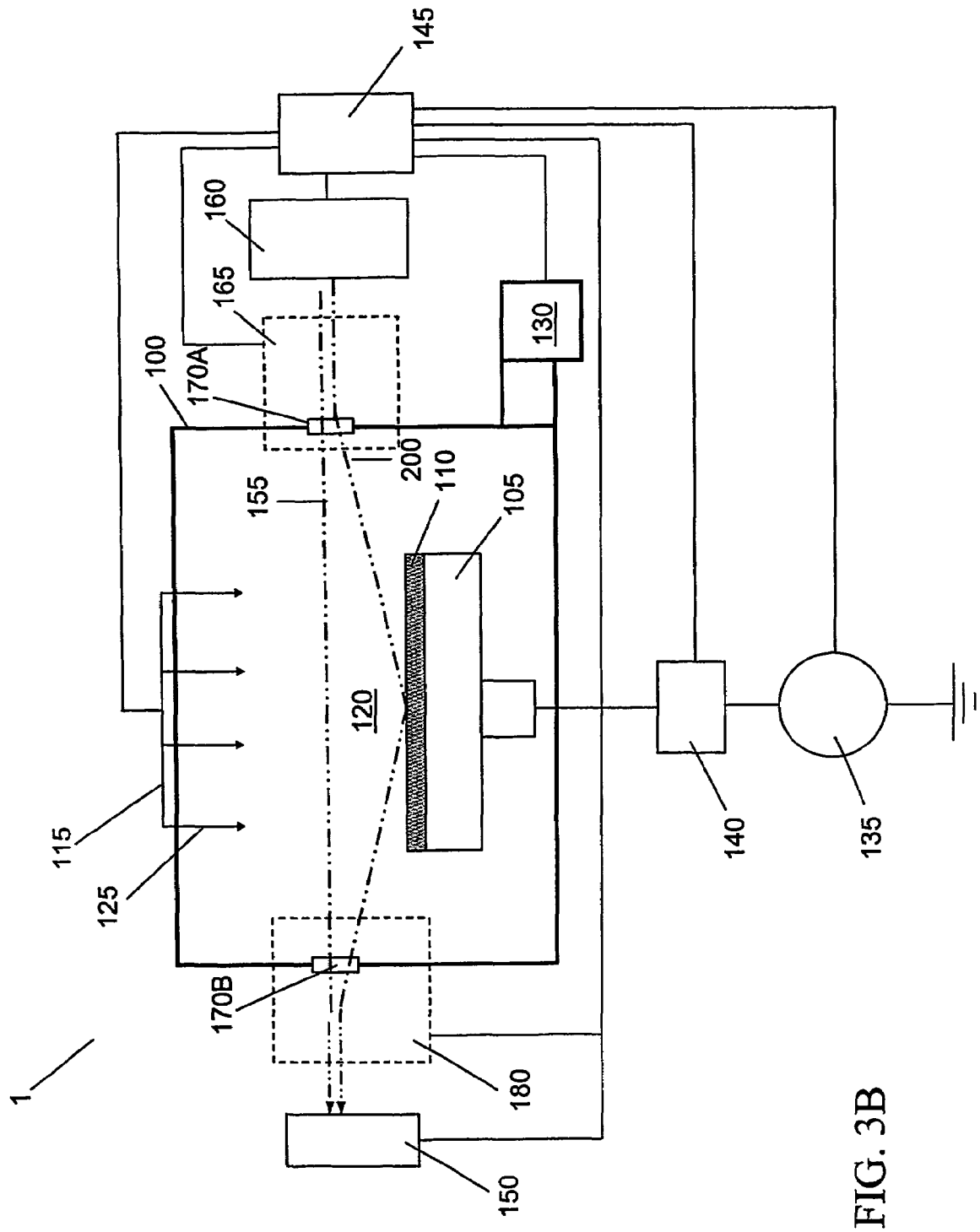
FIG. 3B is a simplified block diagram of third infrared diagnostic system in communication with a plasma processing system according to the present invention.

FIG. 3A is a simplified block diagram of a third plasma processing system according to the present invention. The setup in FIG. 3A can combine the systems shown in FIGS. 1 and 2 and allow for applying both ITAS (or FT-ITAS) and RAIRS (or FT-RAIRS) to monitor a process gaseous environment and adsorbed substrate species. The optics of the infrared monitoring system can be constructed to enable both modes of operation and will be readily apparent to those skilled in the art. One arrangement for accomplishing this uses a splitter in the optical assembly 165 to split the modulated beam from spectrometer 160 into dual beams and direct dual beams 155 and 200 into the process chamber 100 through one or more transmissive windows. Alternatively, a mechanical beam steering system can be used to select the desired optical path for the modulated beam from spectrometer 160. After traveling through the processing chamber, the dual beams are collected by collection optics 180 and directed onto at least one detector. The resulting electronic signals are read and processed by controller 145. In an alternate embodiment shown in FIG. 3B, a single light source emits two beams itself such that no splitter is needed in optical assembly 160. Moreover, two light sources (not shown) could be used to create the dual beams as well.

Figures 4, 5:
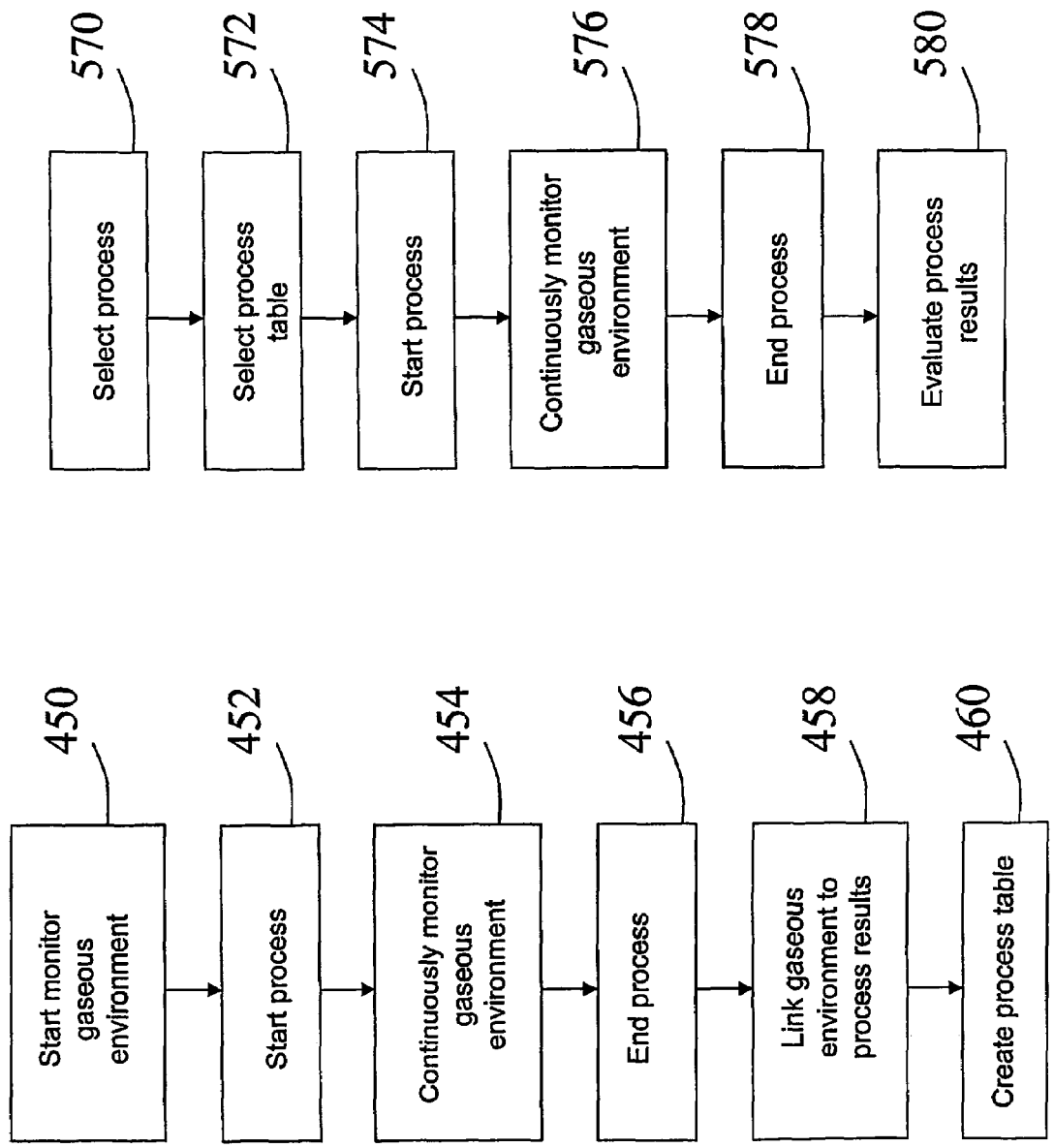
FIG. 4 is a flowchart of a procedure for creating a process table according to the present invention.
FIG. 5 is a flowchart of a procedure for process monitoring according to the present invention.

FIGS. 4 and 5 show flowcharts of procedures that are carried out in process monitoring and control according to the present invention. The flowcharts in FIGS. 4 and 5 refer to using ITAS. Alternatively, the flowcharts in FIGS. 4 and 5 can be applied to monitoring of adsorbed chemical species using RAIRS.

FIG. 4 is a flowchart of a procedure for creating a process table. The flowchart comprises a sequence of steps that establishes a relationship between the gaseous environment for a specific process and physical properties of the processed wafer. The process results can contain physical properties such as etch rate and etch uniformity for an etching process and deposition rate, film uniformity and electrical properties for a deposition processes such as CVD or PVD. Alternatively, the process can involve endpoint detection.

Step 450 starts the monitoring of the gaseous environment associated with a selected process. This step involves establishing a baseline for the monitored signals. For example, the monitored parameters can include pressure, gas flows, gas ratios and gas impurities.

In step 452, the selected process is initiated and run according to a specific recipe. The process is continuously monitored through the gaseous environment in step 454. In step 456, the process is terminated.

In step 458, the physical properties of the process results are linked to one or more gas species or gas ratios present in the gaseous environment during the process. The results in step 458 for multiple runs can be subjected to analysis using statistical process control. The statistical analysis results are used to establish working tolerances for the process. These results are used to create a process table in step 460.

FIG. 5 is a flowchart of a procedure for process monitoring using the process table created in FIG. 4. After a process that leads to a physical property and the corresponding process table 560 from FIG. 4 have been selected in steps 570 and 572, respectively, the process is started in step 574. The gaseous environment is continuously monitored in step 576 during the process. The process is ended in step 578 and the process results are evaluated in step 580.

For example, when an etching process involves endpoint detection, step 576 can be used to indicate when the process endpoint is reached and subsequently the process is terminated in step 578.

In step 580, the process evaluation includes determining a difference between the designated physical property and an actual physical property resulting from process steps 452–456 in FIG. 4. In the case of a process step such as thin film deposition, if the monitored gaseous environment is within a range as determined by the process table, then the actual physical property is within the tolerances of the designated property. On the other hand, if the resulting gaseous environment is outside the range, then the actual physical property is outside the tolerances of the designated physical property. In such a case, the method indicates that the wafer is outside the acceptable limits.

The results of step 580 for multiple runs can be subjected to analysis using statistical process control. The statistical analysis results can be used to continuously revise the process as needed to stay within the established tolerances.

As would be understood by one of ordinary skill in the art, alternate embodiments using plural transmissive windows are also possible. The light source 160 and/or detector may be moved from window to window to measure light transmission at several locations. Moreover, the use of plural light sources substantially simultaneously can allow a plasma to be characterized in multiple dimensions. In addition, transmissive windows may exist in multiple planes to allow three dimensional characterization of a plasma as well. Generally, the multi-point measurement techniques of U.S. Application Ser. No. 60/352,546, filed Jan. 31, 2002 and Ser. No. 10/096,932, filed Mar. 14, 2002, are applicable to transmitting and measuring IR intensities as well.

It should be understood that various modifications and variations of the present invention may be employed in practicing the invention. It is therefore to be understood that, within the scope of the appended claims, the invention may be practiced otherwise than as specifically described herein.

The invention claimed is:

1. An apparatus for detecting infrared light absorption by gaseous species in a processing chamber, comprising:
    an infrared light source;
    a first optical assembly, coupled to a processing chamber, arranged so as to transmit light from the infrared light source into the processing chamber; and
    a second optical assembly arranged so as to receive the light passing through the processing chamber and direct the passed light onto at least one optical sensor.

2. The apparatus according to claim 1, wherein the first optical assembly comprises at least one light transmissive window.

3. The apparatus according to claim 1, wherein the second optical assembly comprises at least one light transmissive window.

4. The apparatus according to claim 1, further comprising means to direct light from the infrared light source along a second optical path that reflects the light off a substrate to be processed in the chamber to the second optical assembly, the second optical assembly arranged so as to receive light along the first and second optical paths and direct the light to the at least one optical sensor.

5. The apparatus according to claim 1, further comprising a controller electrically connected to the at least one optical sensor for receiving and processing electrical signals generated within the at least one optical sensor, so as to provide information pertaining to a spectral content of light incident the at least one optical sensor.

6. The apparatus of claim 1, wherein said infrared light source is a Fourier-transform spectrometer.

7. An apparatus for detecting infrared light absorption by adsorbed species on a substrate in a processing chamber, comprising:
    an infrared light source;
    a first optical assembly, coupled to a processing chamber, arranged so as to direct light from the infrared light source onto a substrate to be processed in the processing chamber; and
    a second optical assembly arranged to receive light reflected off the substrate and direct the reflected light onto at least one optical sensor.

8. The apparatus according to claim 7, wherein the first optical assembly comprises at least one light transmissive window.

9. The apparatus according to claim 7, wherein the second optical assembly comprises at least one light transmissive window.

10. The apparatus according to claim 7, further comprising a controller electrically connected to the optical sensor for receiving and processing electrical signals generated within the optical sensor, so as to provide information pertaining to the spectral content of light incident the optical sensor.

11. The apparatus of claim 7, wherein said infrared light source is a Fourier-transform spectrometer.

12. An apparatus for detecting infrared light absorption by gaseous species and adsorbed substrate species in a processing chamber, comprising:

an infrared light source;
a first optical assembly, coupled to the infrared light source, arranged so as to direct light from the infrared light source along first and second optical paths; and
a second optical assembly arranged so as to receive light along the first and second optical paths and direct the light to at least one optical sensor, wherein the first optical path directs the light through the processing chamber to the second optical assembly, and the second optical path reflects the light of a substrate to be processed in the chamber to the second optical assembly.

13. The apparatus according to claim 12, wherein the first optical assembly comprises at least one light transmissive window.

14. The apparatus according to claim 12, wherein the second optical assembly comprises at least one light transmissive window.

15. An apparatus according to claim 12, further comprising a controller electrically connected to the optical sensor for receiving and processing said electrical signals generated within the at least one optical sensor so as to provide information pertaining to the spectral content of light incident the at least optical sensor.

16. The apparatus of claim 12, wherein said infrared light source is Fourier-transform spectrometer.

17. The apparatus of claim 12, wherein the first optical assembly further comprises a beam splitter for forming plural light beams for the first and second optical paths.

18. A method of measuring infrared light absorption by gaseous species in a processing chamber, the method comprising the steps of:
transmitting light from an infrared light source through a processing chamber;
collecting the transmitted light using an optical assembly;
directing the light onto an optical sensor capable of detecting infrared light;
detecting the light using the optical sensor; and
generating, within the optical sensor, electrical signals representative of the intensity of the light detected.

19. The method of claim 18, the method further comprising the step of using the infrared adsorption by gaseous species to characterize a process step.

20. The method of claim 18, the method further comprising the step of using the infrared adsorption by gaseous species to characterize at least one of a chemical vapor deposition (CVD) process and a physical vapor deposition (PVD) process.

21. The method of claim 18, the method further comprising the step of using the infrared adsorption by gaseous species to characterize at least one of a species to detect an endpoint in at least one of a chamber cleaning process and a chamber conditioning process.

22. The method of claim 18, the method further comprising the step of using the infrared adsorption by gaseous species to characterize at least one of a species to detect an endpoint in a plasma etching process.

23. The method of claim 18, the method further comprising the step of using the infrared adsorption by gaseous species to detect a fault in a plasma etching process.

24. The method as claimed in claim 18, the method further comprising creating a process table containing an acceptable range for the absorption of gaseous species during at least a portion of the at least one process step.

25. The method as claimed in claim 24, the method further comprising the steps of:
performing at least one process step an additional time;
transmitting infrared light in the at least one process step performed the additional time to produce additional infrared absorption of gaseous species;
identifying said additional infrared absorption from the at least one process performed the additional time by measuring light absorbed from said gaseous species;
characterizing the at least one process step performed the additional time using the additional light absorption from said gaseous species from the at least one process step performed the additional time; and
declaring a fault when the at least one process step performed the additional time includes additional light absorption from gaseous species outside of the acceptable range.

26. The method as claimed in claim 18, wherein the method further comprises the steps of:
performing at least one process step an additional time;
transmitting infrared light in the at least one process step performed the additional time to produce additional infrared absorption of gaseous species;
identifying said additional infrared absorption from the at least one process performed the additional time by measuring light absorbed from said gaseous species;
characterizing the at least one process step performed the additional time using the additional light absorption from said gaseous species from the at least one process step performed the additional time; and
determining a change in the absorption of gaseous species over time; and
establishing an endpoint for the at least one process step based on the change in the light absorption of gaseous species over time.

27. The method as claimed in claim 18, wherein the step of detecting comprises detecting light at plural frequencies.

28. A method of measuring infrared light absorption by adsorbed species on a substrate in a processing chamber, the method comprising the steps of:
reflecting infrared light from a substrate in a processing chamber;
collecting the reflected light using an optical assembly;
directing the light onto an optical sensor capable of detecting infrared light;
detecting the light using the optical sensor; and
generating, within the optical sensor, electrical signals representative of the intensity of the light detected.

29. The method of claim 28, the method further comprising the step of using the infrared adsorption by adsorbed substrate species to characterize a process step.

30. The method of claim 28, the method further comprising the step of using the infrared adsorption by adsorbed substrate species to characterize at least one of a chemical vapor deposition (CVD) process and a physical vapor deposition (PVD) process.

31. The method of claim 28, the method further comprising the step of using the infrared adsorption by adsorbed substrate species to characterize at least one of a species to detect an endpoint in at least one of a chamber cleaning process and a chamber conditioning process.

32. The method of claim 28, the method further comprising the step of using the infrared adsorption by adsorbed substrate species to detect at least one of a species to characterize an endpoint in a plasma etching process.

33. The method of claim 28, the method further comprising the step of using the infrared adsorption by adsorbed surface species to detect a fault in a plasma etching process.

34. The method of claim 28, the method further comprising creating a process table containing an acceptable range for the absorption of adsorbed surface species during at least a portion of the at least one process step.

35. The method of claim 28, the method further comprising the steps of:
performing at least one process step an additional time;
transmitting infrared light in the at least one process step performed the additional time to produce additional infrared absorption of adsorbed substrate species;
identifying said additional infrared absorption from the at least one process performed the additional time by measuring light absorbed from said adsorbed substrate species;
characterizing the at least one process step performed the additional time using the additional light absorption from said adsorbed species from the at least one process step performed the additional time; and
declaring a fault when the at least one process steps performed the additional time includes additional light absorption from adsorbed substrate species outside of the acceptable range.

36. The method of claim 28, the method further comprising the steps of:
performing at least one process step an additional time;
transmitting infrared light in the at least one process step performed the additional time to produce additional infrared absorption of adsorbed substrate species;
identifying said additional infrared absorption from the at least one process performed the additional time by measuring light absorbed from adsorbed substrate species;
characterizing the at least one process step performed the additional time using the additional light absorption from said adsorbed substrate species from the at least one process step performed the additional time; and
determining a change in the light absorption of adsorbed substrate species over time; and
establishing an endpoint for the at least one process step based on the change in the light absorption of adsorbed substrate species over time.

37. A method of measuring infrared light absorption by gaseous species and adsorbed species on a substrate in a processing chamber, the method comprising the steps of:
transmitting infrared light through a processing chamber;
using a first optical assembly arranged so as to direct the light along first and second optical paths;
transmitting light along a first optical path through gaseous environment to a second optical assembly;
transmitting light along a second optical path, reflecting the light of a substrate to be processed to the second optical assembly;
collecting the transmitted light along first and second optical paths using a second optical assembly, directing the light onto an optical sensor;
detecting the light using an optical sensor capable of detecting infrared light; and
generating, within the optical sensor, electrical signals representative of the intensity of light incident the first and second optical paths.

* * * * *